(12) United States Patent
Tabe et al.

(10) Patent No.: US 12,249,233 B2
(45) Date of Patent: Mar. 11, 2025

(54) BEAUTY CARE SYSTEM

(71) Applicant: BLOOM CLASSIC CO., LTD, Tokyo (JP)

(72) Inventors: Hayami Tabe, Tokyo (JP); Toshihiro Shibata, Tokyo (JP)

(73) Assignee: BLOOM CLASSIC CO., LTD, Tokyo (JP)

( * ) Notice: Subject to any disclaimer, the term of this patent is extended or adjusted under 35 U.S.C. 154(b) by 386 days.

(21) Appl. No.: 17/878,108

(22) Filed: Aug. 1, 2022

(65) Prior Publication Data

US 2023/0394936 A1    Dec. 7, 2023

(51) Int. Cl.

| | |
|---|---|
| G08B 5/00 | (2006.01) |
| A61H 23/02 | (2006.01) |
| A61N 2/00 | (2006.01) |
| A61N 2/02 | (2006.01) |
| A61N 5/00 | (2006.01) |
| C07K 14/47 | (2006.01) |
| C12N 9/80 | (2006.01) |
| C12N 13/00 | (2006.01) |
| G08B 6/00 | (2006.01) |
| H05K 5/00 | (2025.01) |

(52) U.S. Cl.
CPC .............. G08B 6/00 (2013.01); A61N 2/004 (2013.01); A61N 2/02 (2013.01)

(58) Field of Classification Search
CPC . G08B 6/00; A61N 2/004; A61N 2/02; A61N 5/00; A61H 2201/10; A61H 2201/5007; A61H 23/02; H05K 5/0017; C07K 14/4723; C12N 9/80; C12N 13/00
See application file for complete search history.

(56) References Cited

U.S. PATENT DOCUMENTS

| | | | |
|---|---|---|---|
| 2015/0127074 A1 | | 5/2015 | Thiberg |
| 2021/0401663 A1* | | 12/2021 | Wersland ............ A61N 5/0616 |

FOREIGN PATENT DOCUMENTS

| | | |
|---|---|---|
| CN | 109078266 A | 12/2018 |
| CN | 111744116 A | 10/2020 |
| JP | 2001269382 A | 10/2001 |
| JP | 3123202 U | 7/2006 |
| JP | 2009028269 A | 2/2009 |
| JP | 2020081758 A | 6/2020 |
| JP | 2020137721 A | 9/2020 |
| WO | WO-2019212972 A1 * | 11/2019 ........... A61B 18/203 |

OTHER PUBLICATIONS

Japan Patent Office, Decision of Refusal for Japanese Application No. 2022-089769, Dated: Feb. 1, 2024.
Japan Patent Office, Decision to Grant a Patent for Japanese Patent Application No. 2022-089769, Dated: Jul. 2, 2024.
Japan Patent Office, Notice of Reason for Refusal for Japanese Application No. 2022-089769, Dated: Sep. 19, 2023.

* cited by examiner

*Primary Examiner* — Carrie R Dorna
*Assistant Examiner* — Joshua D Lannu
(74) *Attorney, Agent, or Firm* — Luedeka Neely, P.C.

(57) ABSTRACT

Proposed is a beauty care system including an application means configured to apply a wave at a predetermined frequency to a target person, and a provision means configured to provide a sensation typifying the predetermined frequency to the target person.

5 Claims, 10 Drawing Sheets

Specification includes a Sequence Listing.

Fig. 5

| INPUT CONTENTS | AMPLITUDE |
|---|---|
| H (High) | X (X > 0) cm |
| M (Middle) | Y (0 < Y < X) cm |
| L (Low) | Z (0 < Z < Y) cm |

AMPLITUDE DATA

Fig. 6

| INPUT CONTENTS | DURATION |
|---|---|
| T1 | UNIT TIME 25% |
| T2 | UNIT TIME 50% |
| T3 | UNIT TIME 75% |

DURATION DATA (A) COMPARATIVE EXAMPLE 1   (B) COMPARATIVE EXAMPLE 2   (C) IMPLEMENTATION EXAMPLE 1

BEAUTY CARE SYSTEM

TECHNICAL FIELD

The present invention relates to a beauty care system.

BACKGROUND ART

There has been known a beauty care system capable of obtaining a beauty care effect on, for example, the skin or the like of a target person by applying (emitting) an electromagnetic wave or the like to the target person (for example, Patent Document 1). With the technology disclosed in Patent Document 1, a condition for emitting the electromagnetic wave to a patient is determined on the basis of information resulting from consultation with the patient.

DOCUMENT OF RELATED ART

Patent Document (Patent Document) Japanese Patent Application Publication No. 2020-81758

DISCLOSURE

Technical Problem

Incidentally, it is difficult to perceive by sight or the like a wave, such as electromagnetic wave, that is used in this beauty care system. For this reason, there is a concern that, during beauty care treatment, a target person who undergoes the beauty care treatment will not perceive application of a wave to himself/herself, particularly, at which frequency a wave is applied to himself/herself.

An objective of the present invention, which is made in view of the above-mentioned problem, is to provide a beauty care system in which a target person can easily perceive information relating to a frequency of a wave that is applied to the target person.

Technical Solution

In order to solve the above-mentioned problem, according to an aspect of the present invention, there is provided a beauty care system including an application means configured to apply a wave at a predetermined frequency to a target person; and a provision means configured to provide a sensation typifying the predetermined frequency to the target person.

Advantageous Effects

With a beauty care system according to the present invention, a target person can easily perceive information relating to a frequency of a wave that is applied to the target person.

DESCRIPTION OF DRAWINGS

FIG. 5 is a diagram illustrating an example of a configuration of amplitude data.

FIG. 6 is a diagram illustrating an example of a configuration of a duration data.

MODE FOR INVENTION

An embodiment of the present invention will be described in detail below with reference to the accompanying drawings. However, the present invention is not limited to this embodiment that is exemplary.

(1) Basic Configuration of a Beauty Care System

Figure 1:
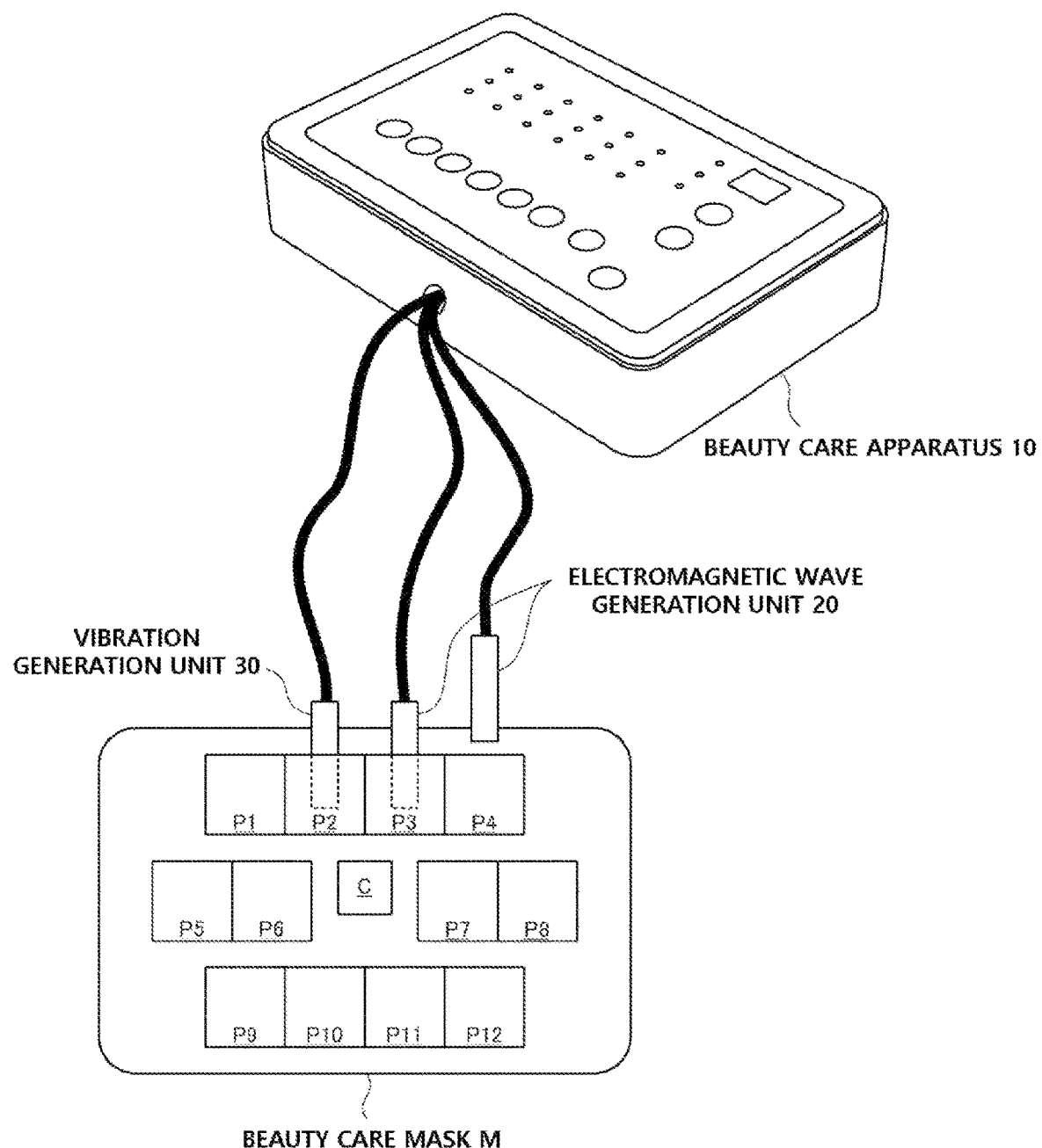
FIG. 1 is a view schematically illustrating a basic configuration of a beauty care system according to an embodiment of the present invention.

FIG. 1 is a view schematically illustrating a basic configuration of a beauty care system according to an embodiment of the present invention. The beauty care system according to the embodiment, as illustrated in FIG. 1, is configured with a box-shaped beauty care apparatus 10, one or more electromagnetic wave generation units 20, and one or more vibration generation units 30. The beauty care apparatus 10, the electromagnetic wave generation unit 20, and the vibration generation unit 30 are connected to each other with a cable for transmitting and receiving a signal. In the present embodiment, the beauty care apparatus 10 is configured in such a manner as to apply a wave at a predetermined frequency to a target person who receives beauty care treatment and to provide a sensation typifying the predetermined frequency to the target person.

In an example illustrated in FIG. 1, each of the electromagnetic wave generation unit 20 and the vibration generation unit 30 is connected to the beauty care apparatus 10, but each of the electromagnetic wave generation unit 20 and the vibration generation unit 30 is accommodated in one casing (for example, a probe casing or the like). It is noted that the casing may be connected to the beauty care apparatus 10 with one cable. At this point, the electromagnetic wave generation unit 20 and the vibration generation unit 30 may be separately controlled by the beauty care apparatus 10 through one common cable, and may be controlled by the beauty care apparatus 10 through individual cables, respectively, that are accommodated in one single cable. In this case, since each of the electromagnetic wave generation unit 20 and the vibration generation unit 30 is accommodated in the casing, it is possible that the wave (here, an electromagnetic wave) at the predetermined frequency and the sensation (here, vibration) typifying the predetermined frequency are generated from one casing. Accordingly, using the casing, the wave at the predetermined frequency and the sensation typifying the predetermined frequency can be perceived more easily.

Each of the electromagnetic wave generation unit 20 and the vibration generation unit 30 is configured in such a manner as to be worn by the target person during the beauty care treatment. Specifically, each of the electromagnetic wave generation unit 20 and the vibration generation unit 30 is configured in such a manner as to be insertable into any one of a plurality of pockets (in an example in FIG. 1, 12 pockets P1 to P12) mounted on an outer surface of a beauty care mask M wearable on the face of the target person. Accordingly, not only can the electromagnetic wave generated by the electromagnetic wave generation unit 20 be applied to the target person, but the vibration generated from the vibration generation unit 30 can also be provided to the target person. At this point, the beauty care mask M is shaped in a manner as to possibly cover the human face from the forehead to the chin and between the two cheeks, and a rectangular cutout C for nasal breathing is formed in a center portion of the beauty care mask M. It is noted the beauty care mask M, for example, may be configured using the technology disclosed in Japanese Utility Model Registration No. 3123202.

In the present embodiment, the electromagnetic wave generation unit 20 includes at least one electrode (in the example illustrated in FIG. 1, two electrodes) that generates the electromagnetic wave at the predetermined frequency. Accordingly, using at least one electrode, the electromagnetic wave at the predetermined frequency can be applied to the target person. At this point, the frequency of the electromagnetic wave generated from each of one or more electrodes may vary in response to a signal (for example, electric current, a predetermined signal, or the like) received from the beauty care apparatus 10 through the cable. Furthermore, the electromagnetic wave generation unit 20 may include a control circuit that controls the frequency of the electromagnetic wave generated from each of one or more electrodes, in response to the signal received from the beauty care apparatus 10 through the cable. It is noted that the electromagnetic waves generated from two or more electrodes may be the same or vary in frequency among two or several electrodes or among all electrodes.

In the present embodiment, the vibration generation unit 30 includes at least one vibration motor (in the example illustrated in FIG. 1, one vibration motor) that generates vibration at a frequency that corresponds to the predetermined frequency. Accordingly, using at least one vibration motor, the vibration at the frequency that corresponds to the predetermined frequency can be provided to the target person. At this point, a frequency of vibration generated from each of one or more vibration motors may vary in response to the signal (for example, the electric current, the predetermined control signal, or the like) received from the beauty care apparatus through the cable. Furthermore, amplitude of the vibration generated from one or more vibration motors or a duration of the vibration generated therefrom may vary in response to the signal received from the beauty care apparatus 10 through the cable.

Moreover, the vibration generation unit 30 may include a control circuit that controls the frequency, the amplitude, and the duration of the vibration generated from each of one or more vibration motors, in response to the signal received from the beauty care apparatus 10 through the cable. It is noted that the vibration generated from two or more vibration motors may be the same or vary in frequency, amplitude, and duration among two or several vibration motors or among all vibration motors.

(2) Configuration of the Beauty Care Apparatus

Figure 2:
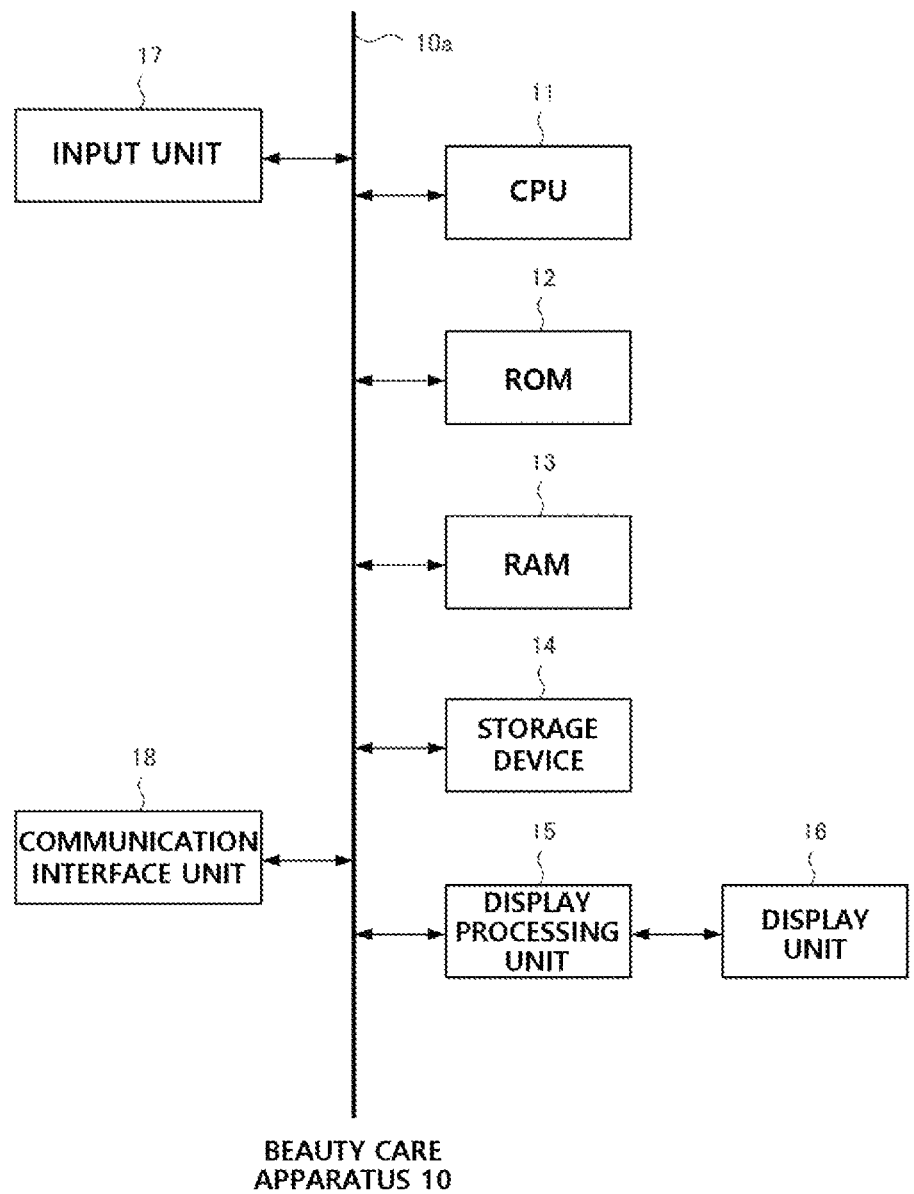
FIG. 2 is a block diagram illustrating a configuration of a beauty care apparatus.
Figure 3:
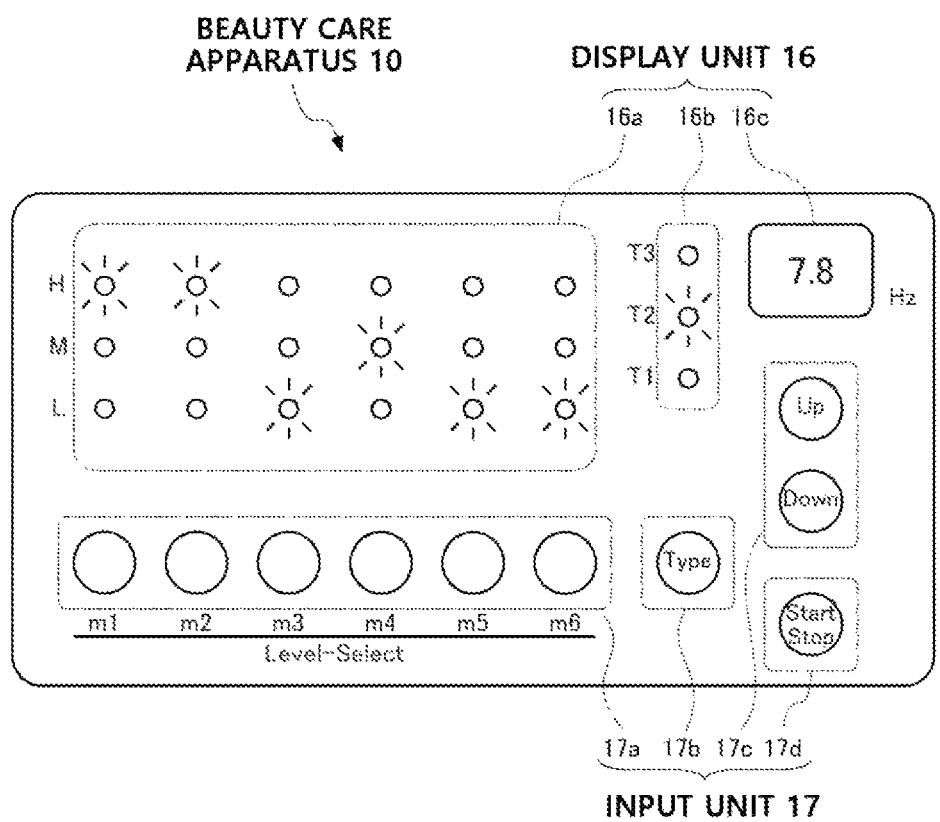
FIG. 3 is a plan view illustrating the beauty care apparatus.

A configuration of the beauty care apparatus 10 according to the present embodiment is described with reference to FIGS. 2 and 3. FIG. 2 is a block diagram illustrating an internal configuration of the beauty care apparatus 10. FIG. 3 is a plan view illustrating the beauty care apparatus 10 according to the present embodiment.

As illustrated in FIG. 2, the beauty care apparatus 10 is configured with a central processing unit (CPU) 11, a read only memory (ROM) 12, a random access memory (RAM) 13, a storage device 14, a display processing unit 15, a display unit 16, an input unit 17, and a communication interface unit 18. A bus 10a for transmitting a control signal or a data signal of each constituent element is provided.

When the beauty care apparatus 10 is powered on, the CPU 11 loads various programs stored in the ROM 12 or the storage device 14 onto the RAM 13 and executes the loaded programs. According to the present embodiment, the CPU 11 reads and executes the program stored in the ROM 12 or the storage device 14, and thus realizes functions of a frequency information acquisition means 41, an amplitude information acquisition means 42, a duration information acquisition means 43, an application means 44, and a provision means 45 (illustrated in FIG. 4) that will be described below.

Examples of the storage device 14 may include non-volatile storage devices, such as a flash memory, a solid state drive (SSD), a magnetic storage device (for example, a hard disk driver (HDD), a floppy disk (a registered trademark), a magnetic tape, or the like), and an optical disk, and volatile storage devices, such as a RAM. Stored in the storage device 14 are programs to be executed by the CPU 11 or data to be referred to by the CPU 11. Furthermore, stored in the storage device 14 are amplitude data (illustrated in FIG. 5) and duration data (illustrated in FIG. 6) that will be described below.

The display processing unit 15 displays display data given from the CPU 11 on the display unit 16. In the present embodiment, the display unit 16 is provided on an upper surface of the beauty care apparatus 10. As illustrated in FIG. 3, the display unit 16 includes an amplitude display unit 16a on which a magnitude (an amplitude level) of vibration generated from the vibration generation unit 30 is displayed, a duration display unit 16b on which a length of a generation duration for at least one of an electromagnetic wave and vibration is displayed, and a frequency display unit 16c on which a frequency of an electromagnetic wave generated from the electromagnetic wave generation unit 20 is displayed.

In the present embodiment, the amplitude display unit 16a is configured with a plurality of lamps (in an example in FIG. 3, 18 lamps) that are arranged in such a manner as to express amplitude levels of each of a plurality of vibration generation units 30 (as illustrated as 6 vibration generations units m1 to m6 in the example in FIG. 3), as three levels, that is, high (H), middle (M), and low (L) levels. Furthermore, the duration display unit 16b is configured with a plurality of lamps (in the example in FIG. 3, three lamps) that are arranged in such a manner as to express lengths of the generation duration for at least one of an electromagnetic wave from the electromagnetic wave generation unit 20 and vibration from each of the vibration generation units 30, as three levels, that is, T1, T2, and T3 (here, T3>T2>T1>0). Moreover, the frequency display unit 16c is configured with a liquid crystal display (LCD) on which the frequency of the electromagnetic wave is displayed.

It is noted that each of the amplitude display unit 16a and the duration display unit 16b may be configured with an LCD and that the amplitude display unit 16a, the duration display unit 16b, and the frequency display unit 16c may be all configured with one LCD.

In the present embodiment, the input unit 17 is provided on the upper surface of the beauty care apparatus 10. As illustrated in FIG. 3, the input unit 17 includes an amplitude input unit 17a for inputting the magnitude (the amplitude level) of the vibration that is generated from the vibration generation unit 30, a duration input unit 17b for inputting the length of the generation duration for at least one of the electromagnetic wave and the vibration, a frequency input unit 17c for inputting the frequency of the electromagnetic wave that is generated from the electromagnetic wave generation unit 20, and an instruction input unit 17d for inputting an instruction to start or stop generating the electromagnetic wave and the vibration.

In the present embodiment, the amplitude input unit 17a is configured with a plurality of buttons (here, 6 buttons) that are arranged in such a manner as to correspond to a plurality of vibration generation units 30 (herein, 6 vibration generation units), respectively. Each time any one button is pushed down, the vibration generation unit 30 that is associated with the pushed-down button switches from one amplitude level to another in this order: amplitude levels H, M, L, H and so forth. Furthermore, the duration input unit 17b is configured with one button. Each time the button is pushed down, at least one of the electromagnetic wave from the electromagnetic wave generation unit 20 and the vibration from each of the vibration generation units 30 switches to one length of the generation duration to another in this order: lengths T1, T2, T3, T1, and so forth. Moreover, the frequency input unit 17c is configured with a first button for increasing the frequency of the electromagnetic wave and a second button for decreasing the frequency of the electromagnetic wave. Each time the first button is pushed down, the frequency of the electromagnetic wave is incremented by a predetermined value (for example, 0.1 Hz, 1 Hz, or the like). Each time the second button is pushed down, the frequency of the electromagnetic wave is decremented by a predetermined value (for example, 0.1 Hz, 1 Hz, or the like). At this point, the frequency of the electromagnetic wave may be arbitrarily set within a predetermined range (for example, within a range of 0.1 to 30 Hz, or the like). Furthermore, the instruction input unit 17d is configured with one button. Each time the one button is pushed down, each of the electromagnetic wave and the vibration is toggled between a generated state and a non-generated state. It is noted that, in a case where the instruction input unit 17d starts to generate the electromagnetic wave and the vibration, the generating of the electromagnetic wave and the vibration may be automatically stopped after a predetermined time (for example, 10 minutes or the like) elapses. Furthermore, the frequency of the electromagnetic wave that is to be applied when the electromagnetic wave starts to be generated, for example, may be set to be a predetermined frequency (a Schumann frequency described below) or may be arbitrarily selected from among multiple different frequencies (including the Schumann frequency described below) using a predetermined button or the like (omitted from the drawings).

The input unit 17 includes an interface circuit for recognizing pushing-down (operation) of the button of each of the amplitude input unit 17a, the duration input unit 17b, the frequency input unit 17c, and the instruction input unit 17d, as input and thus outputting a result of the recognition to the CPU 11.

It is noted that in a case where the beauty care apparatus 10 is an apparatus employing a touch panel input technique, the input unit 17 may receive input in accordance with the touch panel technique by mostly touching a display screen with the human finger or a pen. At this point, the touch panel input technique may be a known technique, such as an electrostatic capacity technique.

Furthermore, in a case where the beauty care apparatus 10 is an apparatus that is capable of receiving voice input, the input unit 17 may be configured in such a manner as to include a microphone for voice input and may include an interface circuit for outputting voice data input through an external microphone to the CPU 11.

The communication interface unit 18 includes an interface circuit for transmitting and receiving a signal to and from each of the electromagnetic wave generation unit 20 and the vibration generation unit 30 through the cable.

(3) Outline of Each Function of the Beauty Care System

Figure 4:
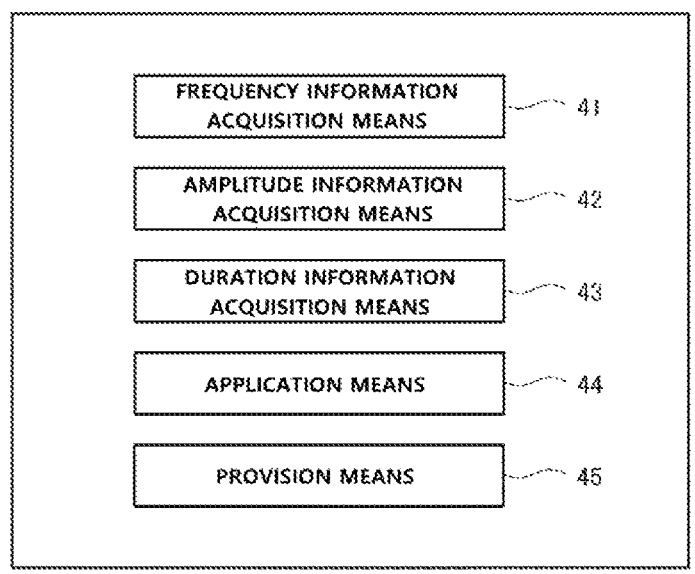
FIG. 4 is a functional block diagram that is referred to for description of a function of fulfilling a principal role in the beauty care system.

A function realized in the beauty care system according to the present embodiment is described with reference to FIG. 4. FIG. 4 is a functional block diagram that is referred to for description of a function of fulfilling a principal role in the beauty care system according to the present embodiment. In the functional block diagram in FIG. 4, the application means 44 and the provision means 45 correspond to a principal configuration of the beauty care system according to the present invention. The other means (the frequency information acquisition means 41, the amplitude information acquisition means 42, and the duration information acquisition means 43) are constituent elements that are not necessarily required, but serves to make the beauty care system according to the present embodiment more preferable.

The frequency information acquisition means 41 has a function of acquiring information relating to a frequency of an electromagnetic wave (a wave) that is applied to the target person.

A function of the frequency information acquisition means 41 is realized, for example, as follows. For example, in a case where the electromagnetic wave and the vibration start to be generated by pushing down the instruction input unit 17d of the input unit 17, the CPU 11 of the beauty care apparatus 10 acquires an initial value of the frequency (for example, the Schumann frequency (for example, 7.8 Hz) described below or the like) of the electromagnetic wave that is generated from the electromagnetic wave generation unit 20, as a value of the frequency of the electromagnetic wave that is applied to the target person. At this point, an initial value of the frequency of the electromagnetic wave may be stored in the RAM 13 or the storage device 14. Furthermore, the CPU 11 may acquire the frequency of the electromagnetic wave that is applied to the target person by incrementing or decrementing by a predetermined value each time the first button or the second button of the frequency input unit 17c of the input unit 17 is pushed down. It is noted that the CPU 11 may store a value of the frequency of the electromagnetic wave that is applied to the target person, in the RAM 13 or the storage device 14.

The amplitude information acquisition means 42 has a function of acquiring information relating to amplitude of vibration that is generated from the vibration generation unit 30.

A function of the amplitude information acquirement means 42 is realized, for example, as follows. For example, in the case where the electromagnetic wave and the vibration start to be generated by pushing down the instruction input unit 17d of the input unit 17, by access to the amplitude data illustrated in FIG. 5, the CPU 11 of the beauty care apparatus 10 may acquire an initial value (for example, X (X>0) cm or the like that corresponds to the amplitude level "H") of amplitude of vibration of each vibration generation unit 30, as a value of the amplitude of the vibration that is generated from the vibration generation unit 30. At this point, the amplitude data are data that are created in a state where the amplitude (in an example in FIG. 5, X cm, Y cm, and Z cm (0<Z<Y<Z) of the vibration that is generated from the vibration generation unit 30 is associated with each of the amplitude levels (in the example in FIG. 5, H, M, and L) that are input using the amplitude input unit 17a of the input unit 17. Furthermore, when, among a plurality of buttons of the amplitude input unit 17a of the input unit 17, a button corresponding to any one of the vibration generation units 30 is pushed down, the CPU 11 may acquire a value (X, Y, or Z) of the amplitude corresponding to the amplitude level (H, M, or L), switching to which occurs in response to pushing down the corresponding button, as the amplitude of the vibration that is generated from any one of the vibration generation units 30. It is noted that the CPU 11 may store the value of the amplitude of the vibration of each of the plurality of vibration generation units 30 in, for example, the RAM 13 or the storage device 14.

The duration information acquisition means 43 has a function of acquiring information relating to the generation duration for at least one of the electromagnetic wave from the electromagnetic wave generation unit 20 and the vibration from the vibration generation unit 30.

A function of the duration information acquisition means 43 is realized, for example, as follows. For example, in the case where the electromagnetic wave and the vibration start to be generated by pushing down the instruction input unit 17d of the input unit 17, by access to the duration data illustrated in FIG. 6, the CPU 11 of the beauty care apparatus 10 may acquire an initial value (for example, "25% (for example, 2.5 seconds) of an unit time (for example, 10 seconds)" corresponding to duration "T1") of the generation duration (here, the generation durations for the electromagnetic wave and the vibration) for at least one of the electromagnetic wave and the vibration, as a value of the generation duration for at least one of the electromagnetic wave and the vibration. In this case, each time the unit time elapses, at least one of the electromagnetic wave and the vibration is generated within a duration that corresponds to 25% of the unit time. At this point, the duration data are data that are created in a state where the generation duration (in an example in FIG. 6, "25% of the unit time", "50% of the unit time", and "75% of the unit time") for at least one of the electromagnetic wave and the vibration is associated with each of the durations (in the example in FIGS. 6, T1, T2, and T3) that are input using the duration input unit 17b of the input unit 17. Furthermore, when a button of the duration input unit 17b of the input unit 17 is pushed down, the CPU 11 may acquire a value ("25% of the unit time", "50% of the unit time", or "75% of the unit time) of a duration corresponding to a duration (T1, T2, or T3), switching to which occurs in response to pushing down the button, as a value of the generation duration for at least one of the electromagnetic wave and the vibration. It is noted that the CPU 11 may store the value of the generation duration in, for example, the RAM 13 or the storage device 14.

It is noted that a case where the generation duration for at least one of the electromagnetic wave and the vibration is divided into three stages is described as one example, but that the generation duration may be divided into two stages or into four or more stages. Furthermore, a case where the generation duration for at least one of the electromagnetic wave and the vibration is expressed as a predetermined percentage of the unit time is described here as one example, but the generation duration, for example, may be expressed as a predetermined numerical value (for example, 10 seconds, 20 seconds, 30 seconds, or the like). Moreover, the generation duration for the electromagnetic wave may be configured in such a manner as to be the same among the electromagnetic wave generation units 20 and may be configured in such a manner as to vary among two or more electromagnetic wave generation units 20. Furthermore, the generation duration for the vibration may be configured in such a manner as to be the same among the vibration generation units 30 and may be configured in such a manner as to vary among two or more vibration generation units 30.

The application means 44 has a function of applying an electromagnetic wave (a wave) at a predetermined frequency to the target person. At this point, the electromagnetic wave (the wave) at the predetermined frequency may be applied to the cell of the target person. Furthermore, the application means 44 may apply the electromagnetic wave (the wave) at the predetermined frequency to the target person by generating the electromagnetic wave at the predetermined frequency from the electromagnetic wave generation unit 20. Accordingly, using the electromagnetic wave generation unit 20, it is possible that the electromagnetic wave at the predetermined frequency is applied to the target person.

At this point, the predetermined frequency may be a Schumann resonance frequency (for example, 7.8 Hz). It is noted that the Schumann resonance is an electromagnetic resonance phenomenon where resonance and sympathetic vibration take place with the limited dimensions of the earth, and are stationary over the surface of the earth. Schumann resonance frequencies, when listed starting from the lowest, are approximately 7.8 Hz, 14.1 Hz, 20.3 Hz, 26.4 Hz, and 32.4 Hz. According to a desired aspect of the present embodiment, the Schumann resonance frequency of the electromagnetic wave (the wave) that is applied to the cell of the target person may range from 7.7 to 7.9 Hz, from 13.9 to 14.3 Hz, from 20.0 to 20.6 Hz, and from 26.0 to 26.8 Hz. Among these ranges, the range from 7.7 to 7.9 Hz and the range from 13.9 to 14.3 Hz are preferable, and particularly, the range from 7.7 to 7.9 Hz is preferable.

Preferably, for example, the following effects may be obtained by applying the wave at the Schumann resonance frequency to the cell.

(1) The application of the wave at the Schumann resonance frequency to the cell can enhance skin defense functions, such as a bacteria destroying function, an immuno-regulation function, an anti-inflammation function, and a wound healing function, through an operation of facilitating expression of an antibacterial peptide.

(2) The application of the wave at the Schumann resonance frequency to the cell can enhance the skin defense functions, such as a cell migration function, a wound-induced innate immunity function, an epidermis re-epithelization function, a granulation tissue formation function, a neovascularization function, and a wound healing function, through an operation of facilitating expression of sirtuin 1.

(3) The application of the wave at the Schumann resonance frequency to the cell can enhance the wound healing function through an operation of migrating the cell and/or an operation of proliferating the cell.

(4) The application of the wave at the Schumann resonance frequency to the cell can facilitate the expression of sirtuin 1 and can enhance the skin defense functions, such as the cell migration function, the wound-induced innate immunity function, the epiderm re-epithelization function, the granulation tissue formation function, the neovascularization function, and the wound healing function, through an operation of inhibiting expression of miR-181a (SEQ ID NO: 1) and the operation of inhibiting expression of miR-181b (SEQ ID NO: 2).

(5) The application of the wave at the Schumann resonance frequency to the cell can enhance a function of proliferating the cell, through an operation of inhibiting expression of miR-132 (SEQ ID NO: 3).

(6) The application of the wave at the Schumann resonance frequency to the cell can enhance a function of healing inflammatory skin diseases, such as psoriasis, hypertrophic scarring, common warts, and thermal injury, through an operation of facilitating expression of miR-145 (SEQ ID NO: 6), an operation of facilitating expression of miR-4654 (SEQ ID NO: 7), an operation of inhibiting expression of miR-647 (SEQ ID NO: 4), and an operation of inhibiting expression of miR-1973 (SEQ ID NO: 5).

At this point, miRNAs, the expression of each of which is modulated by the application of the wave at the Schumann resonance frequency, are shown in Table 1. It is noted that miRBase in Table 1 is a primary on-line database on miRNAs (http://www.mirbase.org) that is managed by the University of Manchester in the UK. The sequence data of the miRNAs is also incorporated into this application by reference to the Sequence Listing XML file with name P21-1144_ST26.xml, created on Oct. 7, 2022, with file size 12,453 bytes.

TABLE 1

| miRNA | miRBase ID | miRBase accession number | Arrangement | Arrangement number |
|---|---|---|---|---|
| miR-181a (SEQ ID NO: 1) | Hsa-miR-181a-2-3p | MIMAT0004558 | accacugaccg uugacuguacc | Arrangement number 1 |
| miR-181b (SEQ ID NO: 2) | Hsa-miR-181b-2-3p | MIMAT0031893 | cucacugauca augaaugca | Arrangement number 2 |
| miR-132 (SEQ ID NO: 3) | Hsa-miR-132-3p | MIMAT0000426 | uaacagucuac agccauggucg | Arrangement number 3 |
| miR-647 (SEQ ID NO: 4) | Hsa-miR-647 | MIMAT0003317 | guggcugcacu cacuuccuuc | Arrangement number 4 |
| miR-1973 (SEQ ID NO: 5) | Hsa-miR-1973 | MIMAT0009448 | accgugcaaag guagcaua | Arrangement number 5 |
| miR-145 (SEQ ID NO: 6) | Hsa-miR-145-5p | MIMAT0000437 | guccaguuuuc ccaggaauccc u | Arrangement number 6 |
| miR-4654 (SEQ ID NO: 7) | Has-miR-4654 | MIMAT0019720 | ugugggaucug gaggcaucugg | Arrangement number 7 |

Furthermore, the wave that is applied to the cell may be a rectangular wave or may be a sinusoidal wave. The rectangular wave is preferable in terms of obtaining a good effect at the cell level.

It is noted that an effect that can be obtained in a case where the wave at the Schumann resonance frequency is applied to the cell is described in implementation examples described below.

Moreover, the application means 44 may apply to the target person an electromagnetic wave (a wave) at a frequency corresponding to information acquired on the basis of the function of the frequency information acquisition means 41. Accordingly, on the basis of the acquired information, it is possible that an electromagnetic wave at an arbitrary frequency is applied to the target person.

Furthermore, the application means 44 may generate the electromagnetic wave from the electromagnetic wave generation unit for a generation duration corresponding to information acquired on the basis of the function of the duration information acquisition means 43. Accordingly, on the basis of the acquired information, it is possible that the electromagnetic wave is applied to the target person within an arbitrary generation duration.

A function of the application means 44 is realized, for example, as follows. For example, in the case where the electromagnetic wave and the vibration start to be generated by pushing down the instruction input unit 17d of the input unit 17, the CPU 11 of the beauty care apparatus 10 generates a signal (for example, electric current, a control signal, or the like) for generating an electromagnetic wave at a frequency corresponding to an initial value of a frequency of an electromagnetic wave that is stored in the RAM 13 or the storage device 14 and transmits the generated signal to each of the electromagnetic wave generation units 20 through the communication interface unit 18 and the cable. In this manner, the electromagnetic wave at the frequency corresponding to the initial value (for example, the Schumann resonance frequency (for example 7.8 Hz)) of the frequency is generated from each of the electromagnetic wave generation units 20 and is applied to the target person.

Furthermore, when information relating to the frequency of the electromagnetic wave that is applied to the target person is acquired on the basis of the function of the frequency information acquisition means 41, the CUP 11 may generate a signal for generating an electromagnetic wave at a frequency corresponding to a value of a frequency that is stored in the RAM 13 or the storage device 14 and may transmit the generated signal to each of the electromagnetic wave generation units 20 through the communication interface unit 18 and the cable. In this manner, an electromagnetic wave at a frequency corresponding to an arbitrary frequency that is input using the frequency input unit 17c is generated from each of the electromagnetic wave generation units 20 and is applied to the target person.

Moreover, when information relating to a generation duration for the electromagnetic wave from the electromagnetic wave generation unit 20 is acquired on the basis the function of the duration information acquisition means 43, the CPU 11 may generate a signal for generating an electromagnetic wave for a generation duration that is stored in the RAM 13 or the storage unit 14 and may transmit the generated signal to each of the electromagnetic wave generation units through the communication interface unit 18 and the cable. In this manner, an electromagnetic wave is generated from each of the electromagnetic wave generation units 20 for an arbitrary generation duration that is input using the duration input unit 17b and is applied to the target person.

The provision means 45 has a function of providing a sensation typifying a predetermined frequency to the target person. Furthermore, the provision means 45 may provide the sensation typifying the predetermined frequency to the target person by generating the vibration at the frequency corresponding to the predetermined frequency from the vibration generation unit 30 worn by the target person.

Accordingly, with a vibration frequency of the vibration generation unit 30 in accordance with the predetermined frequency, the target person can easily perceive the frequency of the electromagnetic wave that is applied to himself/herself.

Moreover, the provision means 45 may provide to the target person a sensation typifying the frequency corresponding to the information acquired on the basis of the function of the frequency information acquisition means 41. Accordingly, on the basis of the acquired information, it is possible that a sensation typifying an arbitrary frequency is provided to the target person.

Furthermore, the provision means 45 may generate from the vibration generation unit 30 vibration having amplitude corresponding to the information acquired on the basis of the function of the amplitude information acquirement means 42. Accordingly, since vibration having arbitrary amplitude is provided to the target person on the basis of the acquired information, for example, vibration having appropriate amplitude can be provided to each of the plurality of target persons.

Furthermore, the provision means 45 may generate amplitude from the vibration generation unit 30 for the generation duration corresponding to the information acquired on the basis of the function of the duration information acquisition means 43. Accordingly, on the basis of the acquired information, it is possible that vibration within an arbitrary generation duration is provided to the target person.

A function of the provision means 45 is realized, for example, as follows. For example in the case where the electromagnetic wave and the vibration start to be generated by pushing down the instruction input unit 17d of the input unit 17, the CPU 11 of the beauty care apparatus 10 generates a signal (for example, electric current, a control signal, or the like) for generating vibration at the frequency corresponding to the initial value of the frequency of the electromagnetic wave that is stored in the RAM 13 or the storage device 14 and transmits the generated signal to each of the vibration generation units 30 through the communication interface unit 18 and the cable. In this manner, the vibration at the frequency corresponding to the initial value (for example, the Schumann resonance frequency (for example, 7.8 Hz)) of the frequency is generated from each of the vibration generation units 30 and is provided to the target person.

At this point, in the present embodiment, a case where the frequency of the vibration that is generated from each of the vibration generation units 30 is the same as the frequency of the electromagnetic wave that is generated from the electromagnetic wave generation unit 20 is described as one example, but the frequency of the vibration that is generated from each of the vibration generation units 30 may be different from the frequency of the electromagnetic wave that is generated from the electromagnetic wave generation unit 20. For example, the frequency of the vibration may be a predetermined multiple of the frequency of the electromagnetic wave and may be a value obtained by substituting the frequency of the electromagnetic wave into a predetermined computation equation.

Furthermore, when the information relating to the frequency of the electromagnetic wave that is applied to the target person is acquired on the basis of the function of the frequency information acquisition means 41, the CPU 11 may generate a signal for generating vibration at the frequency corresponding to the value of the frequency that is stored in the RAM 13 or the storage device 14 and may transmit the generated signal to each of the vibration generation units 30 through the communication interface unit 18 and the cable. In this manner, the vibration at the frequency corresponding to the arbitrary frequency that is input using the frequency input unit 17c is generated from each of the vibration generation units 30 and is provided to the target person.

Moreover, when the information relating to the amplitude of the vibration that is generated from any vibration generation unit 30 of the plurality of vibration generation units 30 is acquired on the basis of the function of the amplitude information acquirement means 42, the CPU 11 may generate a signal (for example, electric current, a control signal, or the like) for causing the any vibration generation unit 30 to generate amplitude corresponding to a value of amplitude that is stored in the RAM 13 or the storage device 14 and may transmit the generated signal to the any vibration generation unit 30 through the communication interface unit 18 and the cable. In this manner, vibration having arbitrary amplitude that is input using the amplitude input unit 17a is generated from each of the vibration generation units 30 and is provided to the target person.

Furthermore, when information relating to a generation duration for the vibration from the vibration generation unit 30 is acquired on the basis of the function of the duration information acquisition means 43, the CPU 11 may generate a signal for generating vibration for the generation duration that is stored in the RAM 13 or the storage device 14 and may transmit the generate signal to each of vibration generation units 30 through the communication interface unit 18 and the cable. In this manner, for an arbitrary generation duration that is input using the duration input unit 17b, vibration is generated from each of the vibration generation units 30 and is provided to the target person.

Figure 7:
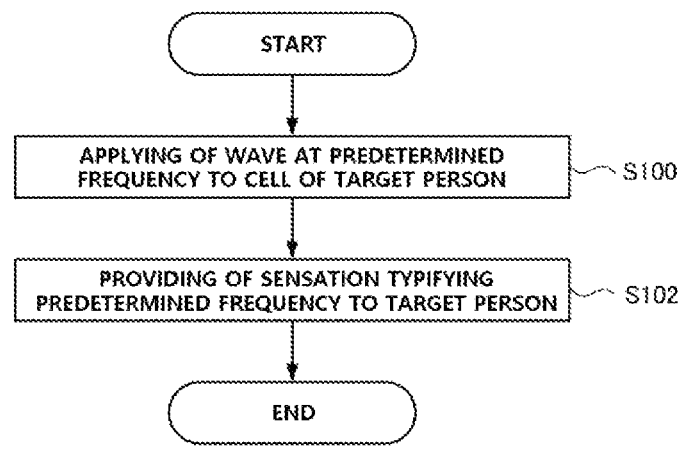
FIG. 7 is a flowchart illustrating an example of principal processing by the beauty care system according to the embodiment of the present invention.

(4) Flow of Principal Processing by the Beauty Care System According to the Present Embodiment Next, an example of a flow for principal processing that is performed by the beauty care system according to the present embodiment is described with reference to a flowchart in FIG. 7.

On the basis of the function of the application means 44, the CPU 11 of the beauty care apparatus 10 applies an electromagnetic wave (a wave) at a predetermined frequency to the target person, for example, using the electromagnetic wave generation unit 20 or the like (Step S100). At this point, the CPU 11 may apply the electromagnetic wave at the predetermined frequency to the target person by generating the electromagnetic wave at the predetermined frequency from the electromagnetic wave generation unit 20. Furthermore, the predetermined frequency may be the Schumann resonance frequency (for example 7.8 Hz). Moreover, the CPU 11 may generate an electromagnetic wave from the electromagnetic wave generation unit 20 for the generation duration corresponding to the information acquired on the basis of the function of the duration information acquisition means 43.

Next, the CPU 11 of the beauty care apparatus 10 provides a sensation typifying the predetermined frequency to the target person on the basis of the function of the provision means 45 (Step S102). At this point, the CPU 11 may provide the sensation typifying the predetermined frequency to the target person by generating the vibration at the frequency corresponding to the predetermined frequency from the vibration generation unit 30 worn by the target person. Furthermore, the CPU 11 may generate from the vibration generation unit 30 the vibration having the amplitude corresponding to the information acquired on the basis of the function of the amplitude information acquirement means 42. Moreover, the CPU 11 may generate amplitude from the vibration generation unit 30 for the generation duration corresponding to the information acquired on the basis of the function of the duration information acquisition means 43.

It is noted that the CPU 11 of the beauty care apparatus 10 may apply to the target person the electromagnetic wave (the wave) at the frequency corresponding to the information acquired on the basis of the function of the frequency information acquisition means 41. Furthermore, the CPU 11 may provide to the target person a sensation typifying the frequency corresponding to the information acquired on the basis of the function of the frequency information acquisition means 41.

As described above, with the beauty care system according to the present embodiment, since the sensation (the vibration) typifying the frequency of the electromagnetic wave (the wave) that is to be applied to the target person is provided to the target person, the target person can easily perceive at which frequency the electromagnetic wave is applied to himself/herself.

It is noted that a program for causing a computer to realize the functions of the means 41 to 45 described above may be stored on a computer-readable storage medium. The storage medium on which the program is recorded may be the ROM 12, the RAM 13, or the storage device 14 of the beauty care apparatus 10 illustrated in FIG. 2. Furthermore, the storage medium, for example, may be a CD-ROM or the like that is readable by being inserted into, for example, a program readable device, such as a CD-ROM driver. Moreover, the storage medium may be a magnetic tape, a cassette tape, a flexible disk, an MO/MD/DVD, or the like and may be a semiconductor memory.

The embodiment is described above to provide a disclosure for an easy understanding of the present invention, and therefore imposes any limitation on the present invention. Therefore, each constituent element disclosed in the embodiment described above is intended to include all design amendments thereto or equivalents thereof that fall within the technical scope of the present invention.

For example, in the embodiment, a case where the application means 44 applies the electromagnetic wave (the wave) at the predetermined frequency (for example, the Schumann resonance frequency) to the target person is described above as one example, but it should be noted that according to an aspect of the present invention, the application means 44 also applies to the target person an electromagnetic wave (a wave) at any frequency in a predetermined frequency bandwidth in which the predetermined frequency is included.

Furthermore, in the embodiment, a case where the electromagnetic wave generation unit 20 and the vibration generation unit 30 are inserted into the pockets P1 to P12 in the beauty care mask M that is to be worn on the face of the target person and thus is worn by the target person is described above as one example, but the present invention is not limited to this case. For example, the electromagnetic wave generation unit 20 and the vibration generation unit 30 may be configured in such a manner that they are possibly directly worn on the face or the like of the target person without using the beauty care mask M.

Moreover, in the embodiment, a case where the vibration at the frequency corresponding to the frequency of the electromagnetic wave is provided, as a sensation, to the target person, is described above, but the present invention is not limited to this case. For example, voice information, visual information (for example, image information), or the like that corresponds to the frequency of the electromagnetic wave may be provided, as a sensation, to the target person.

Furthermore, in the embodiment, a case where the frequency information acquisition means 41, the amplitude information acquisition means 42, and the duration information acquisition means 43 acquire information by inputting the information using the input unit 17 is described above as one example, but the present invention is not limited to this case. For example, at least one of the frequency information acquisition means 41, the amplitude information acquisition means 42, and the duration information acquisition means 43 may acquire information by receiving the information transmitted from an apparatus connected to the beauty care apparatus 10 in such a manner as to possibly communicate therewith through a communication network, such as the Internet or a local area network (LAN).

Figure 8:
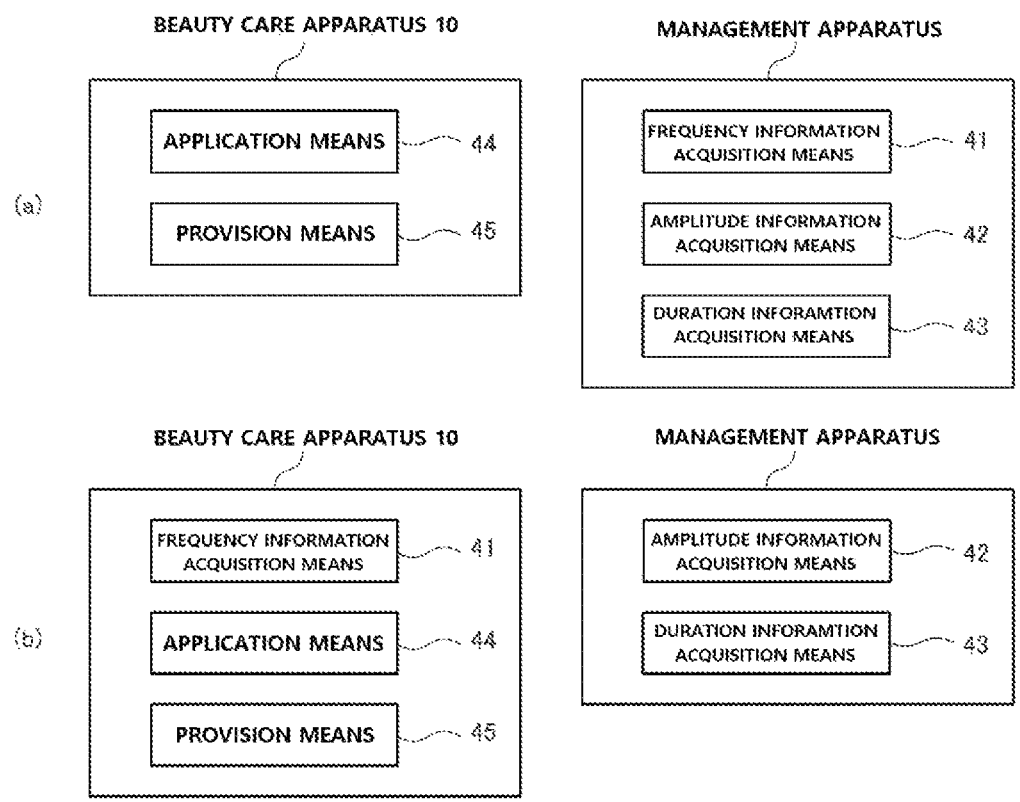
FIG. 8 is a diagram illustrating an example of distributing each function of the beauty care system between the beauty care apparatus and a management apparatus.

Moreover, in the embodiment, a configuration in which respective functions of the frequency information acquisition means 41, the amplitude information acquisition means 42, the duration information acquisition means 43, the application means 44, and the provision means 45 are realized by the beauty care apparatus 10 is employed, but the present invention is not limited to this configuration. For example, a configuration in which the function of at least one of the means 41 to 45 described above is realized by a management apparatus (for example, an all-purpose personal computer, a server computer, or the like) that is connected to the beauty care apparatus 10 in such a manner as to possibly communicate therewith through the communication network, such as the Internet or the local area network (LAN) may be employed. In this case, each function in the functional block diagram illustrated in FIG. 4, as illustrated in FIGS. 8(a) and 8(b), may be arbitrarily distributed between the beauty care apparatus 10 and the management apparatus.

Furthermore, the management apparatus may be configured in such a manner as to communicate with a plurality of beauty care apparatuses 10. For example, information (for example, at least one of information relating to a frequency of a wave, information relating to amplitude of vibration, and information relating to a duration for the vibration) acquired by the management apparatus may be transmitted to each of the beauty care apparatuses 10. Accordingly, using the management apparatus, it is possible that operation of each of the plurality of beauty care apparatuses 10 is controlled.

[Implementation Examples]

Implementation examples will be described, and the present invention is not limited to any of these implementation examples described below.

Experimental Example 1: Experiment with the Operation of Migrating the Cell

Normal Human Epidermal Keratinocytes (NHEK) derived from a child as a single donor (the number of successive subcultures: 2 to 4, manufactured by PromoCell GmbH) were cultured at a temperature of 37° C. in the presence of 5% $CO_2$, using Keratinocyte Growth Medium2 (KGM2, manufactured by PromoCell). After cultivated, 2 ml of NHEK per dish was planted in each 35 mm dish at a concentration of $12 \times 10^4$ cells/mL. NHEK were cultivated until a confluent state was entered and then were cultivated for another 24 hours (G0 period). Cross-lines were drawn with a 200 μL pipette tip in the 35 mm dish and thus cells were peeled off. Then, NHEK were cleaned with medium culture (KGM2) and were cultivated for another 24 hours. This case was defined as Comparative Example 1 (n=3).

Furthermore, when peeling off the cell and after 24 hours of culturing, NHEK were cultured in the same manner as in Comparative Example 1, except that NHEK were left unattended for 10 minutes on a generator (product name: "CF-FM783-BA", and operating current: 1 mV, manufactured by Walfront LLC) generating a pulse at an extremely low frequency of 7.83 Hz and that an electromagnetic wave was then applied (n=3). This case was defined as Implementation Example 1.

Moreover, after peeling-off of cells, NHEK were cultured for 24 hours using the medium culture (KGM2) containing a final 0.1 μg/mL concentration of mycoplasma-induced synthetic diacylated lipopeptide (Fibroblast-Stimulating Lipopeptide-1 (FSL-1), manufactured by Adipogen Life Science). NHEK were cultured with the other conditions being the same as in Comparative Example 1 (n=3). It is known that diacylated lipopeptide, recognized as a Toll-like receptor (TLR), facilitates production of the antibacterial peptide. This case was defined as Comparative Example 2.

Figure 9:
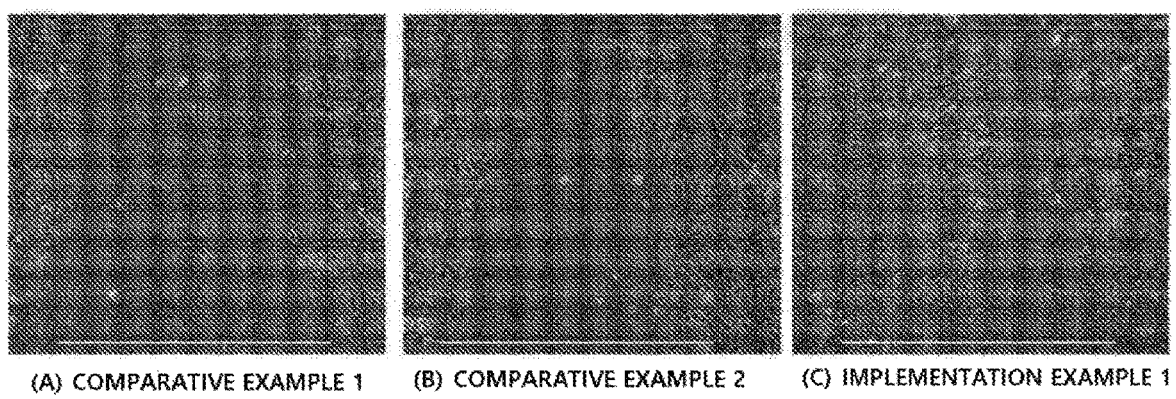
FIG. 9 is photographs showing results typifying an operation of migrating the cell. It is noted that the bar on a lower portion of the photograph has a length of 0.6 mm.

In Implementation Example 1 and Comparative Examples 1 and 2, after 24 hours of culturing, a state of the vicinity of a groove created by reeling off cells with a pipette tip was observed with a microscope. Photographs obtained through a microscope are shown in FIG. 9.

An excellent operation of migrating the cell was recognized in Implementation Example 1 (C) where an electromagnetic wave at a frequency of 7.83 Hz (the wave at the Schuman resonance frequency) was applied than in Comparative Example 1(A) and Comparative Example 2(B).

Experimental Example 2: An Experiment with an Operation of Facilitating Expression of β-Defensin 2 and Ctericidine After the experiment with the operation of migrating the cell was conducted (observation with a microscope) in Experimental Example 1, in each of Implementation Example 1 and Comparative Examples 1 and 2, the medium culture is removed, and cleaning was performed with a phosphate buffer solution. Subsequently, 1 ml of 1% sodium dodecyl sulfate (manufactured by Nippon Gene) was added and the cell was collected. This cell suspension was sufficiently stirred with a vortex, and then 180 μL was gathered. 1 μL of 1% KOH (manufactured by Nacalitesk Co., Ltd) and 20 μL of 20 mg/mL Proteinase K Solution (manufactured by Thermo Fisher Scientific Inc.) were added to the resulting cell suspension, and the result were incubated at a temperature of 37° C. for 15 minutes. 100 μL of RNA Clean XP (manufactured by Beckman Coulten Inc.) was added to each result of the incubation, and the result, after stirred, was left at rest on a magnet stand for 5 minutes. A supernatant liquid was removed. The result was cleaned two times with 85% ethanol, and then was dried for 10 minutes. 30 μL of Nuclease-FreeWater (manufactured by Thermo Fisher Scientific Inc.) was added. The result was left at rest on the magnet stand for 5 minutes, and the supernatant liquid was used as an RNA solution.

At a temperature of 0° C., in 200 μL of PCR tube (with Clear Dome Cap, Manufactured by Bio-Rad Laboratories, Inc.), Nuclease-free water and Super Script IV VILO Master Mix (manufactured by Thermo Fisher Scientific Inc.) were prepared at a ratio of 2.5 to 1, the result was stirred with a vortex, and then 14.0 μL was dispensed to each of the separate PCR tubes. 6.0 μL of the RNA solution obtained as described above was added to this result. Reverse transcription reaction (25° C. for 10 minutes, 50° C. for 10 minutes, and 85° C. for 5 minutes) was performed using a thermal cycler (product name: "T100 Thermal Cycler", manufactured by Bio-Rad Laboratories, Inc.). Thus, cDNA solution was obtained.

Taqman Gene Expression Assays (manufactured by Thermo Fisher Scientific Inc.) was used for multiplication of cDNA. Specifically, the same was also applied to cathelicidin (CAMP, Assay ID: Hs00189038_m1) and p-actin (ACTB, Assay ID: Hs99999903_m1) as an endogenous control, using Taqman Gene Expression Assays (DEFB4A/DEFB4B, Assay ID: Hs00175474_m1) containing a primer and a probe that are capable of multiplying β-defensin2. TaqPath qPCR Master Mix, CG (manufactured by Thermo Fisher Scientific Inc.) and Nuclease-free water were prepared at a ratio of 10:5 with respect to Taqman Gene Expression Assays1, and the result was placed in a Nuclease-free tube, was stirred with a vortex, and then was spun down. 16.0 μL of the result was dispensed to each PCR tube (with White Flat Cap, manufactured by Bio-Rad Laboratories, Inc.), and 4.0 μL of the cDNA solution (Implementation Example 1, Comparative Example 1, or Comparative Example 2) was added to each result of the dispensing. The result was stirred by pipetting and vortexing and then was spun down.

Using these samples, real-time PCR (product name: "C1000 Touch Thermal Cycler", manufactured by Bio-Rad Laboratories, Inc.) was performed. The real-time PCR was implemented in the following PCR conditions: at a temperature of 25° C. for 2 minutes, at a temperature of 95° C. for 20 seconds, at a temperature of 95° C. for 3 seconds (1), and at a temperature of 60° C. for 30 seconds (2) (40 cycles from (1) to (2)). An amount of expression of β-defensin2 and an amount of expression of cathelicidin were standardized with an amount of expression of β-activation. Expression facilitation ratios of β-defensin2 and cathelicidin were calculated as relative values with respect to an average value of amounts of expression of genes in Comparative Example 1 (non-processing) standardized, the average value being defined as 1. The results are shown in Table 2.

TABLE 2

| | Expression facilitation ratio | |
|---|---|---|
| | β-defensin2 | cathelicidin |
| Comparative Example 1 | 1 | 1 |
| Comparative Example 2 | 13.76 | 1.79 |
| Implementation Example 1 | 26.32 | 34.00 |

From Table 2, it can be seen that the expression of each of β-defensin2 and cathelicidin was facilitated more in Implementation Example 1 where an electromagnetic wave (the wave at the Schumann resonance frequency) at a frequency of 7.83 Hz was applied to the cell than in Comparative Example 1 (non-processing). Furthermore, the expression of β-defensin2 and the expression of cathelicidin were also more facilitated in Implementation Example 1 than in Comparative Example 2 where diacylated lipopeptide was added.

Experimental Example 3: An Experiment with the Operation of Proliferating the Cell Normal Human Epidermal Keratinocytes (NHEK) derived from a child as a single donor (the number of successive subcultures: 2 to 4, manufactured by PromoCell GmbH) were cultured at a temperature of 37° C. in the presence of 5% $CO_2$, using Keratinocyte Growth Medium2 (KGM2, manufactured by PromoCell GmbH). After cultured, 100 μL of NHEK per well was planted in each of the 96 well plates at a concentration of $4\times10^4$ cells/mL and was cultured for 96 hours.

After 24 hours of culturing, 48 hours of culturing, and 72 hours of culturing, NHEK were left unattended for 10 minutes on the generator (product name: "CF-FM783-BA", and operating current: 1 mV, manufactured by Walfront LLC) generating a pulse at an extremely low frequency of 7.83 Hz and then an electromagnetic wave was applied (n=6). A case where an electromagnetic wave (a rectangular wave) having predetermined amplitude was continuously applied for 10 minutes was defined as Implementation Example 2. Furthermore, a case where an electromagnetic wave that is a sinusoidal wave (having the same amplitude as the rectangular wave) was applied for 10 minutes was defined as Implementation Example 3. Moreover, a non-processing well was also prepared as a control (n=6), and this case was defined as Comparative Example 3.

After 96 hours of culturing, a culture solution was removed, cleaning was performed using a phosphate buffer solution (manufactured by Sigma-Aldrich Japan Co LlC), 100 μL of 50 μg/mL Neutral Red (NR) (manufactured by Nakalitesk company) was added to each well, and then culturing was performed for 3 hours. The NR liquid was removed, 200 μL of fixing liquid (1% formaldehyde) was added, and thus the cell was fixed. The fixing liquid was removed, 100 μL of extraction liquid (1% acetic acid, 50% 2-propanol) was added to each well, and NR entrapped in the cell was extracted. An absorbance of 540 nm was measured with a microplate reader (product name: "Immuno Mini NJ-2300", manufactured by NaruGenk International Co.). Values of the absorbance of 540 nm are shown in Table 3. A cell proliferation ratio was calculated as a relative value with respect to an average value of the absorbance of 540 nm in Comparative Example 3 (non-processing), the average value being defined as 1. The results are shown in Table 3.

successive subcultures: 2 to 4, manufactured by PromoCell GmbH) were cultured at a temperature of 37° C. in the presence of 5% $CO_2$, using Keratinocyte Growth Medium2 (KGM2, manufactured by PromoCell). After cultured, 5 mL of NHEK was planted in each T25 flask at a concentration of $3\times10^4$ cells/mL (n=3 to 5) and was further cultured for another 72 hours. This case was defined as Comparative Example 4.

Furthermore, after planted, after 24 hours, 48 hours, and 72 hours of culturing, NHEK were left unattended for 10 minutes on the generator (product name: "CF-FM783-BA", and operating current: 1 mV, manufactured by Walfront LLC) generating a pulse at an extremely low frequency of 7.83 Hz, and then an electromagnetic wave was applied. This case was defined as Implementation Example 4.

After 72 hours of culturing, in the same manner as in Experimental Example 2, in Implementation Example 4 and Comparative Example 4, the cell was collected, an RNA solution was obtained, then reverse transcription was performed, and a cDNA solution was obtained.

Taqman Gene Expression Assays (manufactured by Thermo Fisher Scientific Inc.) was used for multiplication of cDNA. Specifically, β-actin (ACTB, assay ID: Hs99999903_ml) was used as sirtuin 1 (SIRT1, assay ID: Hs01009006) and endogenous control. Then, real-time PCR took place in the same manner as in Experimental Example 2. An amount of expression of sirtuin 1 was standardized with an amount of expression of β-actin. An expression facilitation ratio of sirtuin 1 was calculated as a relative value with respect to an average value of amounts of expression of genes in Comparative Example 4 (non-processing) standardized, the average value being defined as 1. Results of the calculation are shown in Table 4.

TABLE 3

|  | Absorbance of 540 nm | | | | | | Average | SD | Cell Growth Ratio |
|---|---|---|---|---|---|---|---|---|---|
| Comparative Example 3 | 0.121 | 0.085 | 0.144 | 0.216 | 0.279 | 0.178 | 0.171 | 0.070 | 1 |
| Implementation Example 2 | 0.486 | 0.556 | 0.482 | 0.461 | 0.500 | 0.397 | 0.480 | 0.047 | 2.81 |
| Implementation Example 3 | 0.211 | 0.192 | 0.208 | 0.188 | 0.135 | 0.258 | 0.199 | 0.040 | 1.16 |

From Table 3, it can be recognized that cell proliferation was facilitated more in Implementation Examples 2 and 3 in which an electromagnetic wave (the wave at the Schumann resonance frequency) at a frequency of 7.83 Hz is applied to the cell than in Comparative Example 3 (non-processing), that the operation of proliferating the cell was detected 2.81 times more in Implementation Example 2 than in Comparative Example 3, and that the operation of proliferating the cell was detected 1.16 times more in Implementation Example 3 than in Comparative Example 3.

Experimental Example 4: An Experiment with the Operation of Facilitating Expression of Sirtuin 1

Normal Human Epidermal Keratinocytes (NHEK) derived from a child as a single donor (the number of

TABLE 4

|  | Expression Facilitation Ratio Sirtuin 1 |
|---|---|
| Comparative Example 4 | 1 |
| Implementation Example 4 | 4.9 |

From Table 4, it can be recognized that the expression of sirtuin 1 was facilitated more in Implementation Example 4 where an electromagnetic wave (the wave at the Schumann resonance frequency) at a frequency of 7.83 Hz was applied to the cell than in Comparative Example 4 (non-processing).

Experimental Example 5: miRNA Analysis of Exosomes 5 m of NHEK were planted in each T25 flask at a concentration of 3×10⁴ cells/ml (n=2). After 24 hours, 48 hours, and 72 hours of culturing, NHEK were left unattended for 10 minutes on the generator (product name: "CF-FM783-BA", and operating current: 1 mV, manufactured by Walfront LLC) generating a pulse at an extremely low frequency of 7.83 Hz and then an electromagnetic wave was applied. This case was defined as Implementation Example 4. The case where an electromagnetic wave at a frequency of 7.83 Hz was not applied was defined as Comparative Example 5 (non-processing). After 72 hours of culturing, a culture supernatant was provided to ExoQuick-TC (manufactured by System Bioscience LLC.), and thus exosomes were collected. The collected exosomes (n=2) were suspended in 300 µL of PBS, and then were stored at a temperature of −80° C. RNA was extracted from exosomes and then an amount of expression of miRNA was analyzed using an on-assignment analysis service provided by Toray Industries, Inc. In the on-assignment analysis service, labeling was performed with 3D-Gene miRNA Labeling kit (manufactured by Toray Industries, Inc.), hybridization was performed on a 3D-Gene Human miRNA Oligo chip (ver.22 equipped with 2,632 types of miRNA detection probes, and manufactured by Toray Industries, Inc.) at a temperature of 32° C. for 16 hours, and then an image was acquired using a scanner (3D-Gene Scanner 3000, manufactured by Toray Industries, Inc.) and was analyzed using quantization software (3D-Gene Extraction software, manufactured by Toray Industries, Inc.).

A measurement value was adjusted in such a manner that a median of values obtained as a result from measurement was 25 and then was normalized to 75-th percentage of correction values of total 2,632 types. The result of the normalization was defined as an amount of expression of each of the total 2,632 types, and a comparison was made between Implementation Example 5 and Comparative Example 5.

An amount of expression of miR-145-5p (SEQ ID NO: 6) and an amount of expression of miR-4654 (SEQ ID NO: 7), which were at the same level as the background in Comparative Example 5, were remarkably more facilitated in Implementation Example 5. When a correction value in Comparative Example 5 was defined as 1 for comparison in terms of an expression change ratio, the expression of miR-145-5p (SEQ ID NO: 6) was calculated as being 12.19 times as high, and the expression of miR-4654 (SEQ ID NO: 7) was calculated as being 12.40 times as high. MiR-181a-2-3p (SEQ ID NO: 1), miR-181b-2-3p (SEQ ID NO: 2), miR-132-3p (SEQ ID NO: 3), miR-647 (SEQ ID NO: 4), and miR-1973 (SEQ ID NO: 5) have a significant amount of detected expression in Comparative Example 5, but have an amount of expression remarkably reduced to the same level as the background in Implementation Example 5. When a correction value in Implementation Example 5 is defined as 1 for comparison in terms of the expression change ratio, the expression of miR-181a-2-3p (SEQ ID NO: 1) was calculated as being 0.087 times as high, the expression of miR-181b-2-3p (SEQ ID NO: 2) was calculated as being 0.116 times as high, the expression of miR-132-3p (SEQ ID NO: 3) was calculated as being 0.090 times as high, the expression of miR-647 (SEQ ID NO: 4) was calculated as being 0.089 times as high, and the expression of miR-1973 (SEQ ID NO: 5) was calculated as being 0.091 times as high.

Experimental Example 6: Experiment with the Operation of Migrating the Cell

Normal Human Dermal fibroblasts (HF) derived from an adult as a single donor (the number of successive subcultures: 4) were cultured at a temperature of 37° C. in the presence of 5% $CO_2$, using a Dulbecco Modified Eagle Medium (DMEM, manufactured by Nacalai Tesque, Inc.) having a 10% bovine fetus serum. After cultured, 2 ml of HF per dish was placed at a concentration of 2×10⁴ cells/mL in each 35 mm dish. HF were cultured until a confluent state was entered and then was further cultured for 24 hours (GO period). Cross-lines were drawn with a 200 µL pipette tip in the 35 mm dish and thus cells were peeled off. Then, HF were cleaned using a medium (DMEM) and were cultivated for another 24 hours. This case was defined as Comparative Example 6 (n=3).

Furthermore, when the cells were peeled off, the 35 mm dish was left unattended on the top of the electromagnetic wave generation unit 20 of the beauty care apparatus 10 for 10 minutes, and the electromagnetic wave that was a rectangular wave was applied. The application of the electromagnetic wave was performed in a combination of a frequency of 7.8 Hz, a duration T1, T2, or T3, and amplitude L, M, or H.

=Durations=
T1: Repeat of Application of the Electromagnetic Wave for 0.032 Seconds and Non-application thereof for 0.096 Seconds
T2: Repeat of Application of the Electromagnetic Wave for 0.064 Seconds and Non-application thereof for 0.064 Seconds
T3: Repeat of Application of the Electromagnetic Wave for 0.096 Seconds and Non-application thereof for 0.032 Seconds =Amplitude=
L: 0.6 V
M: 1.5 V
H: 2.5 V T1-L, T1-M, and T1-H were defined as Implementation Examples 6, 7, and 8, respectively. T2-L, T2-M, and T2-H were defined as Implementation Examples 9, 10, and 11, respectively. T3-L, T3-M, and T3-H were defined as Implementation Examples 12, 13, and 14, respectively. Culturing was performed in the same manner as in Comparative Example 6 except that the electromagnetic wave was applied (n=3).

Figure 10:
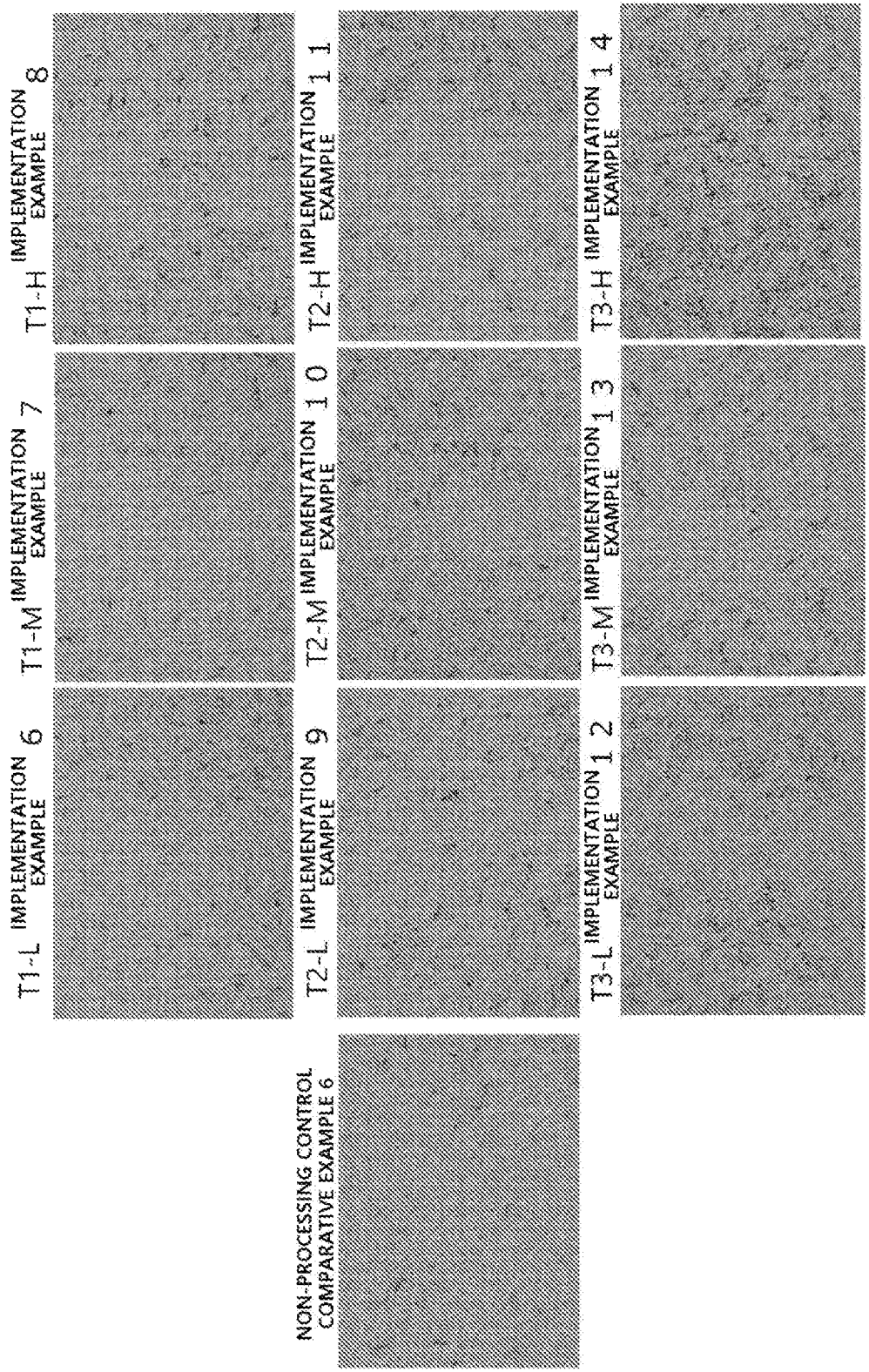
FIG. 10 is photographs showing results typifying an operation of migrating the cell by applying the electromagnetic wave to the cell.

After 24 hours of culturing, cleaning was performed with the phosphate buffer solution, and fixing was performed with 2 mL of methanol (manufactured by FUJIFILM Wako Pure Chemical Corporation). After methanol removal and air drying, staining was performed with 2 mL of 5% Giemsa staining solution (manufactured by Nacalitesk Co., Ltd). After water washing and air drying, in Implementation Examples 6 to 14 and Comparative example 6, states of the vicinity of a groove created by peeling off cells with the pipette tip were photographed. The photographs are shown in FIG. 10.

A more excellent operation of proliferating the cell was recognized in Implementation Examples 6 to 14 in which an electromagnetic wave at a frequency of 7.8 Hz is applied than in Comparative Example 6.

INDUSTRIAL APPLICABILITY

The beauty care system according to the present invention, as described above, for example, can be used suitably for a beauty care service, such as a service for enhancing the skin defense function. Thus, the beauty care system has extremely high industrial applicability.

10: Beauty Care Apparatus
20: Electromagnetic Wave Generation Unit
30: Vibration Generation Unit
41: Frequency Information Acquisition Means
42: Amplitude Information Acquisition Means
43: Duration Information Acquisition Means
44: Application Means
45: Provision Means
M: Beauty Care Mask
Arrangement Table
P21-1144 ST26.xml

The invention claimed is:

1. A beauty care system comprising:
a beauty care apparatus comprising:
 an application means configured to apply a wave at a predetermined frequency to a target person, wherein the predetermined frequency is a Schumann resonance frequency; and
 a provision means configured to provide a tactile sensation typifying the predetermined frequency to the target person; and
a mask configured to be put on a face of the target person and to be connected to the beauty care apparatus, wherein the mask includes a plurality of pockets to contain a vibration generation unit and an electromagnetic wave generation unit,
wherein the beauty care apparatus, the vibration generation unit, and the electromagnetic wave generation unit are connected by at least one cable, wherein the vibration generation unit is inserted into a first pocket of the plurality of pockets of the mask,
wherein the provision means provides the tactile sensation typifying the predetermined frequency to the target person by vibrating the vibration generation unit at a frequency corresponding to the predetermined frequency, and
wherein the application means applies the wave at the predetermined frequency to the target person by generating an electromagnetic wave at the predetermined frequency from the electromagnetic wave generation unit that is inserted into a second pocket of the plurality of pockets of the mask.

2. The beauty care system of claim 1, wherein the beauty care apparatus further comprises:
a duration information acquisition means configured to acquire information relating to a generation duration for the electromagnetic wave from the electromagnetic wave generation unit,
wherein the application means generates the electromagnetic wave from the electromagnetic wave generation unit for the generation duration corresponding to the acquired information.

3. The beauty care system of claim 1, wherein the beauty care apparatus further comprises:
an amplitude information acquisition means configured to acquire information relating to amplitude of vibration at the vibration generation unit,
wherein the provision means vibrates the vibration generation unit with vibration having the amplitude of vibration corresponding to the acquired information.

4. The beauty care system of claim 1, wherein the beauty care apparatus further comprises:
a duration information acquisition means configured to acquire information relating to a generation duration for vibration at the vibration generation unit,
wherein the provision means vibrates the vibration generation unit for the generation duration corresponding to the acquired information.

5. The beauty care system of claim 1, wherein the beauty care apparatus further comprises:
a frequency information acquisition means configured to acquire information relating to a frequency of the wave that is applied to the target person,
wherein the application means applies the wave at the frequency corresponding to the acquired information to the target person, and
wherein the provision means provides the tactile sensation typifying the frequency corresponding to the acquired information to the target person.

* * * * *

```
                              SEQUENCE LISTING

Sequence total quantity: 7
SEQ ID NO: 1            moltype = RNA   length = 22
FEATURE                 Location/Qualifiers
misc_feature            1..22
                        note = hsa-miR-181a-2-3p
source                  1..22
                        mol_type = transcribed RNA
                        organism = Homo sapiens
ncRNA                   1..22
                        ncRNA_class = miRNA
SEQUENCE: 1
accactgacc gttgactgta cc                                                  22

SEQ ID NO: 2            moltype = RNA   length = 20
FEATURE                 Location/Qualifiers
misc_feature            1..20
                        note = hsa-miR-181b-2-3p
source                  1..20
                        mol_type = transcribed RNA
                        organism = Homo sapiens
ncRNA                   1..20
                        ncRNA_class = miRNA
SEQUENCE: 2
ctcactgatc aatgaatgca                                                     20

SEQ ID NO: 3            moltype = RNA   length = 22
FEATURE                 Location/Qualifiers
misc_feature            1..22
                        note = hsa-miR-132-3p
source                  1..22
                        mol_type = transcribed RNA
                        organism = Homo sapiens
ncRNA                   1..22
                        ncRNA_class = miRNA
SEQUENCE: 3
taacagtcta cagccatggt cg                                                  22

SEQ ID NO: 4            moltype = RNA   length = 21
FEATURE                 Location/Qualifiers
misc_feature            1..21
                        note = hsa-miR-647
source                  1..21
                        mol_type = transcribed RNA
                        organism = Homo sapiens
ncRNA                   1..21
                        ncRNA_class = miRNA
SEQUENCE: 4
gtggctgcac tcacttcctt c                                                   21

SEQ ID NO: 5            moltype = RNA   length = 19
FEATURE                 Location/Qualifiers
misc_feature            1..19
                        note = hsa-miR-1973
source                  1..19
                        mol_type = transcribed RNA
                        organism = Homo sapiens
ncRNA                   1..19
                        ncRNA_class = miRNA
SEQUENCE: 5
accgtgcaaa ggtagcata                                                      19

SEQ ID NO: 6            moltype = RNA   length = 23
FEATURE                 Location/Qualifiers
misc_feature            1..23
                        note = hsa-miR-145-5p
source                  1..23
                        mol_type = transcribed RNA
                        organism = Homo sapiens
```

```
ncRNA                   1..23
                        ncRNA_class = miRNA
SEQUENCE: 6
gtccagtttt cccaggaatc cct                                       23

SEQ ID NO: 7            moltype = RNA  length = 22
FEATURE                 Location/Qualifiers
misc_feature            1..22
                        note = hsa-miR-4654
source                  1..22
                        mol_type = transcribed RNA
                        organism = Homo sapiens
ncRNA                   1..22
                        ncRNA_class = miRNA
SEQUENCE: 7
tgtgggatct ggaggcatct gg                                        22
```